United States Patent [19]
Dyke et al.

[11] Patent Number: 5,804,588
[45] Date of Patent: Sep. 8, 1998

[54] QUINOLINE CARBOXANIDES AND THEIR THERAPEUTIC USE

[75] Inventors: Hazel Joan Dyke; John Gary Montana; Christopher Lowe; Hannah Jayne Kendall; Verity Margaret Sabin, all of Cambridge, United Kingdom

[73] Assignee: Chiroscience Limited, United Kingdom

[21] Appl. No.: 859,508

[22] Filed: May 20, 1997

[30] Foreign Application Priority Data

| May 20, 1996 | [GB] | United Kingdom | 9610506 |
| Nov. 7, 1996 | [GB] | United Kingdom | 9623234 |
| Dec. 24, 1996 | [GB] | United Kingdom | 9626883 |
| Apr. 22, 1997 | [GB] | United Kingdom | 9708072 |

[51] Int. Cl.$^6$ .................. C07D 215/00; A61K 31/47
[52] U.S. Cl. ................. 514/314; 514/311; 546/169
[58] Field of Search .............. 546/169; 514/311, 514/314

[56] References Cited

U.S. PATENT DOCUMENTS

| 4,147,694 | 4/1979 | Erickson | 546/169 |
| 4,186,201 | 1/1980 | Erickson | 424/258 |
| 4,238,506 | 12/1980 | Stach et al. | 424/319 |

OTHER PUBLICATIONS

Ghosh et al. Chemical Abstracts, vol. 59, No. 5, Abstract 6364 g–h, Sep. 9,1963.
Merchant et al. Chemical Abstracts, vol. 75, No. 10, Abstract 76,564f, Sep.6,1971.

*Primary Examiner*—Zinna Northington Davis
*Attorney, Agent, or Firm*—Saliwanchik, Lloyd & Saliwanchik

[57] ABSTRACT

The subject invention concerns novel compounds of the general formula (i)

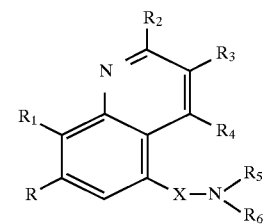

that are useful in treating disease states, such as those states associated with proteins that mediate cellular activity. The compounds of the subject invention can be used, for example, to inhibit tumor necrosis factor and/or phosphodiesterase IV, The subject invention also concerns methods for treating disease states using the compounds of the invention.

28 Claims, No Drawings

QUINOLINE CARBOXAMIDES AND THEIR THERAPEUTIC USE

FIELD OF THE INVENTION

The present invention relates to novel quinolines, and to their formulation and use as pharmaceuticals.

BACKGROUND OF THE INVENTION

EP-A-0498722 discloses quinoline amides as angiotensin $A_2$ an endothelin inhibitor.

Phosphodiesterases (PDE) and Tumour Necrosis Factor (TNF), their modes of action and the therapeutic utilities of inhibitors thereof are described in WO-A-9636595, WO-A-9636596 and WO-A-9636611, the contents of which are incorporated herein by reference The same documents disclose amides having utility as PDE and TNF inhibitors.

SUMMARY OF THE INVENTION

This invention is based on the discovery of novel compounds that can be used to treat disease states, for example disease states associated with proteins that mediate cellular activity, for example by inhibiting tumour necrosis factor and/or by inhibiting phosphodiesterase IV. According to the invention, the novel compounds are of formula (i):

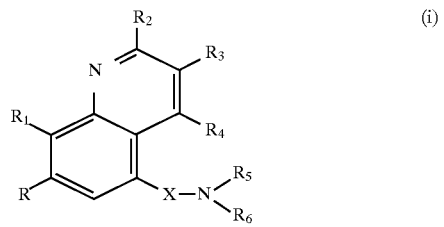

wherein X is CO or CS;
R is H, halogen or alkyl;
$R_1$ represents OH, alkoxy optionally substituted with one or more halogens, or thioalkyl,
$R_2$, $R_3$ and $R_4$ are the same or different and are each H, $R_7$, $OR_{11}$, $COR_7$, $C(=NOR_7)R_7$, alkyl-$C(=NOR_7)R_7$, halogen, $CF_3$, alkyl-$C(=NOH)R_7$, $C(=NOH)R_7$, CN, $CO_2H$, $CO_2R_{11}$, $CONH_2$, $CONHR_7$, $CON(R_7)_2$, $NR_9R_{10}$ or $CONR_{12}R_{13}$ where $NR_{12}R_{13}$ is a heteroyclic ring (such as niorpholinc or piperidine) optionally substituted with one or more $R_{15}$;
$R_5$ represents H, arylalkyl, heteroarylalkyl, heterocycloalkyl, $S(O)_mR_{11}$ or alkyl optionally substituted with one or more substituents chosen from hydroxy, alkoxy, $CO_2R_8$, $SO_2NR_{12}R_{13}$, $CONR_{12}R_{13}$, CN, carbonyl oxygen, $NR_9R_{10}$, $COR_{11}$, and $S(O)_nR_{11}$;
$R_6$ represents aryl, heteroaryl, heterocyclo, arylalkyl, heteroarylalkyl or heterocycloalkyl;
in $R_5$ and/or $R_6$, the aryl/heteroary/heterocyclo portion is optionally substituted with one or more substituents alkyl-$R_{14}$ or $R_{14}$;
$R_7$ represents $R_{11}$ optionally substituted at any position with (one or more) $R_{16}$;
$R_8$ represents H, alkyl, cycloalkyl, arylalkyl, heteroarylalkyl or heterocycloalkyl;
$R_9$ represents H, aryl, heteroaryl, heterocyclo, cycloalkyl, alkyl, arylalkyl, heteroarlalkyl, heterocycloalkyl, alkylcarbonyl, alkoxycarbonyl, arylsulphonyl, heteroarsulphonyl, heterocyclosulphonyl, arylcarbonyl, heteroarylcarbonyl, heterocyclocarbonyl or alkylsulphonyl;
$R_{10}$ represents H, aryl, heteroaryl, heterocyclo, alkyl, cycloalkyl, arylalkyl, heteroarylalkyl or heterocycloalkyl;
$R_{11}$ represents alkyl, cycloalkyl, aryl, heteroaryl, heterocyclo, arylalkyl, heteroarylalkyl or heterocycloalkyl;
$R_{12}$ and $R_{13}$ are the same or different and are each H or $R_{11}$, or $NR_{12}R_{13}$ represents a heterocyclic ring as defined above;
$R_{14}$ represents alkyl (optionally substituted by one or more halogens), cycloalkyl, aryl, heteroaryl, heterocyclo, hydroxy, alkoxy (optionally substituted by one or more halogens), thioalkyl, aryloxy, heteroaryloxy, heterocyclooxy, arylalkyloxy, heteroarylalkyloxy, heterocycloalkyloxy, $CO_2R_6$, $CONR_{12}R_{13}$, $SO_2NR_{12}R_{13}$, halogen, —CN, —$NR_9R_{10}$, $COR_{11}$, $S(O)_nR_{11}$, or (where appropriate) carbonyl oxygen;
$R_{15}$ represents alkyl, aryialkyl or heteroarylalkyl;
$R_{16}$ represents alkyl, OH, $OR_{11}$, $NR_9R_{10}$, CN, $CO_2H$, $CO_2R_{11}$, $CONR_{12}R_{13}$ or $COR_{11}$;
m represents 1–2; and
n represents 0–2; and pharmaceutically-acceptable salts.

Combinations of substituents and/or variables are only permissible if such combinations result in stable compounds.

Description of the Invention

Suitable pharmaceutically-acceptable sats are pharmaceutically-acceptable base salts and pharmaceutically-acceptable acid addition salts. Certain of the compounds of formula (i) which contain an acidic group form base salts. Suitable pharmaceutically-acceptable base salts include metal salts, such as alkali metal salts for example sodium salts, or organic amine salts such as that provided with ethylenediamine.

Certain of the compounds of formula (i) which contain an amino group form acid addition salts. Suitable acid addition salts include pharmaceutically-acceptable inorganic salts such as the sulphate, nitrate, phosphate, borate, hydrochloride and hydrobromide and pharmaceutically-acceptable organic acid addition salts such as acetate, tartrate, maleate, citrate, succinate, benzoate, ascorbate, metbanesulphate, α-ketoglutarate, α-glycerophosphate and glucose-1-phosphate. The pharmaceutically-acceptable salts of the compounds of formula (i) are prepared using conventional procedures.

It will be appreciated by those skilled in the art that some of the compounds of formula (i) may exist in more than one tautomeric form. This invention extends to all tautomeric forms.

It will be appreciated that the compounds according to the invention can contain one or more asymmetrically substituted atoms. The presence of one or more of these asymmetric centers in a compound of formula (i) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as a part of another group includes straight and branched chain alkyl groups containing up to 6 atoms. Alkoxy means an alkyl-O— group in which the alkyl group is as previously described. Aryloxy means an aryl-O— group in which the aryl group is as defined below. Heteroaryloxy means a heteroaryl-O— group and heterocyclooxy means a heterocyclo-O— group in which the heteroaryl and heterocyclo group are as defined below. Arylalkyloxy means an aryl-alkyl-O— group. Alkylamino means an alkyl-N— group in which the alkyl group is as previously defined, arylamino means aryl-N- and heteroarylamino means an heteroaryl-N— group (aryl and heteroaryl defined below). Thioalkyl means an alkyl-S-group. Cycloalkyl includes a non-aromatic cyclic or multicyclic ring system of about 3 to 10 carbon atoms. The cyclic alkyl may optionally be partially unsaturated. Aryl indicates carbocyclic radicals containing about 6 to 10 carbon atoms. Arylalkyl means an aryl-alkyl-group wherein the aryl and alkyl are as described herein. Heteroarylalkyl means a heteroaryl-alkyl group and heterocycloalkyl means a heterocyclo-alkyl group. Alkylcarbonyl means an alkyl-CO— group in which the alkyl group is as previously described. Arylcarbonyl means an aryl-CO— group in which the aryl group is as previously described. Heteroarylcarbonyl means a heteroaryl-CO— group and heterocyclocarbonyl means a heterocyclo-CO— group. Arylsulphonyl means an aryl-$SO_2$— group in which the aryl group is as previously described. Heteroarylsulphonyl means a heteroaryl-$SO_2$— group and heterocyclosulponyl means a heterocyclo-$SO_2$— group. Alkoxycarbonyl means an alkyloxy-CO— group in wich the alkoxy group is as previously desribed. Alkylsulphonyl means an alkyl-$SO_2$— group in which the alkyl group is as previously described, Carbonyl oxygen means a -CO— group. It will be appreciated that a carbonyl oxygen can not be a substituent on an aryl or heteroaryl ring. Carbocyclic ring means about a 5 to about a 10 membered monocyclic or multicyclic ring system which may saturated or partially unsaturated. Heterocyclic ring means about a 5 to about a 10 membered monocyclic or multicyclic ring system (which may saturated or partially unsaturated) wherein one or more of the atoms in the ring system is an element other than carbon chosen from amongst nitrogen, oxygen or sulphur atoms. Heteroaryl means about a 5 to about a 10 membered aromatic monocyclic or multicyclic hydrocarbon ring system in which one or more of the atoms in the ring system is an element other than carbon, chosen from amongst nitrogen, oxygen or sulphur; if desired, a N atom may be in the form of an N-oxide. Heterocyclo means about a 5 to about a 10 membered saturated or partially saturated monocyclic or multicyclic hydrocarbon ring system in which one or more of the atoms in the ring system is an element other than carbon, chosen from amongst nitrogen, oxygen or sulphur. Examples include morpholine and piperidine. Halogen means fluorine, chlorine, bromine or iodine.

Compounds of the invention are useful for the treatment of TNF mediated disease states. "TNF mediated disease or disease states" means any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are considered to be inhibited by compounds of the present invention and thus are herein referred to collectively as "TNF" unless specifically indicated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof.

PDE IV inhibitors are useful in the treatment of a variety of allergic and inflammatory diseases, including, asthma, chronic bronchitis, chronic obstructive airways disease, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, sepsis, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. PDE IV inhibitors may also be useful in the treatment of tardive dyskinesia, ischaemia and Huntingdon's disease. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza adenovirus and the Herpes group of viruses, such as, but not limited to, *Herpes zoster* and *Herpes simplex*.

This invention more specifically relates to a method of treating a mammal, afflicted with a human immunodeficiency virus (HIV), which comprises administering to such mammal an effective TNF inhibiting amount of a compound of Formula (i) or a pharmaceutically-acceptable salt thereof.

The compounds of this invention may also be used in association with the veterinary treatment of animals, other than humans, in need of inhibition of TNF production. TNF mediated diseases for treatment, therapeutically or prophylactically, in animals include disease states such as those noted above, but in particular viral infections, Examples of such viruses include, but are not limited to feline immunodeficiency virus (FIV) or other retroviral infection such as equine infectious anaemia virus, caprine arthritis virus, visna virus, macdi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

The compounds of formula (i) are preferably in pharmaceutically-acceptable form. By pharmaceutically-acceptable form is meant, inter alia, of a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%.

The invention further provides a process for the preparation of a compound of formula (i), in which $R_1$ etc, m and n are as defined above. It will be appreciated that functional groups such as amino, hydroxyl or carboxyl groups present in the various compounds described below, and which it is desired to retain, may need to be in protected forms before any reaction is initiated. In such instances, removal of the protecting group may be the final step in a particular reaction sequence. Suitable protecting groups for such functionality will be apparent to those skilled in the art. For specific details, see Protective Groups in Organic Synthesis, Wiley Interscience, TW Greene. Thus the process for preparing compounds of formula (i) in which $R_3$ contains an —OH comprises of deprotecting (for example by hydrogenolysis or hydrolysis) a compound of formula (i) in which $R_3$ contains an appropriate —OP wherein P represents a suitable protecting group (e.g. benzyl or acetate).

It will be appreciated that where a particular stereoisomer of formula (i) is required, this may be obtained by conventional resolution techniques such as high performance liquid chromatography or the synthetic processes herein described may by performed using the appropriate homochiral starting material.

A process for the preparation of a compound of formula (i) wherein X is CO comprises reaction of an appropriate carboxylic acid of formula (ii) with a suitable amine of formula (iii)

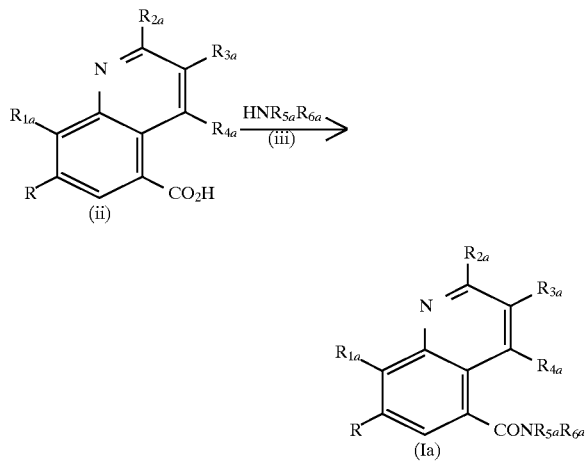

wherein $R_{1a}$ represents $R_1$ as defined in relation to formula (i) or a group convertible to $R_1$ and $R_{2a}$–$R_{6a}$ similarly represent $R_2$–$R_6$ or groups convertible to $R_2$–$R_6$ respectively; and thereafter, if required, converting any group $R_{1a}$ to $R_1$ and/or $R_{2a}$ to $R_2$ and/or $R_{3a}$ to $R_3$ and/or $R_{4a}$ to $R_4$ and/or $R_{5a}$ to $R_5$ and/or $R_{6a}$ to $R_6$. The reaction of a carboxylic acid of formula (ii) with an amine of formula (iii) may be carried out under any suitable conditions known to those skilled in the art. Preferably, the carboxylic acid is converted into an acid chloride, mixed anhydride or other activated intermediate prior to reaction with an amine of formula (iii). Preferably, the reaction with the amine of formula (iii) is carried out in the presence of a suitable base, for example an amine such as triethylamine, preferably in an appropriate solvent such as dichloromethane. In some cases a stronger base, such as sodium hydride, and a polar solvent such as dimethylformamide, will be required, Carboxylic acids of formula (ii) are either commercially available, previously described compounds or are prepared using standard procedures known to those skilled in the art. For example, a carboxylic acid of formula (ii) can conveniently be prepared from an appropriately substituted aminobenzoic acid of formula (iv) and a ketone (or aldehyde) of formula (v) using a Skraup reaction (Z. H. Skraup, Ber. 13: 2086 (1880)). The reaction can be carried out using standard conditions known to those skilled in the art.

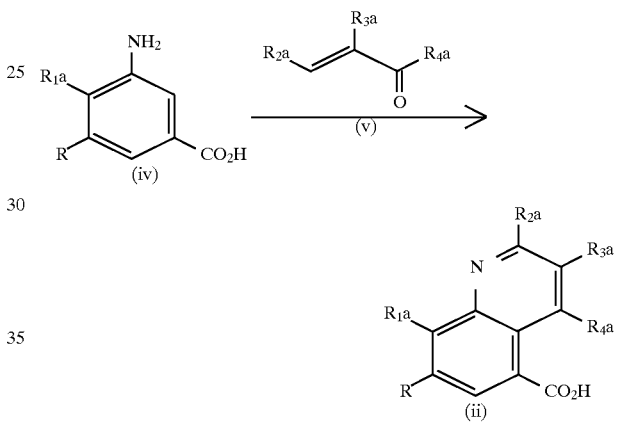

Acids of formula (iv) and ketones (or aldehydes) of formula (v) are either commercially available, previously described compounds or are prepared using standard procedures known to those skilled in the art.

Acids of formula (ii) may alternatively be prepared by carboxylation of bromides of formula (vi). Such carboxylationzs may be carried out using any standard conditions known to those skilled in the art, for example under organometal catalysis (e.g. palladium catalysis). Bromides of formula (vi) may be prepared by bromination of quinolives of formula (vii) under standard conditions know to those skilled in the art, for example by using bromine in methanol. Quinolines of formula (vii) are either commercially available, previously described compounds or are prepared using standard procedures known to those skilled in the art. For example, quinolines of formula (vii) may be conveniently prepared by a Skraup reaction of an appropriate aniline of formula (viii) with a ketone (or aldehyde) of formula (v). An alternative method for the preparation of quinolines of formula (vii) is the Combes reaction (A. Combes, Bull. Soc. Chim. France 49:89 (1888)).

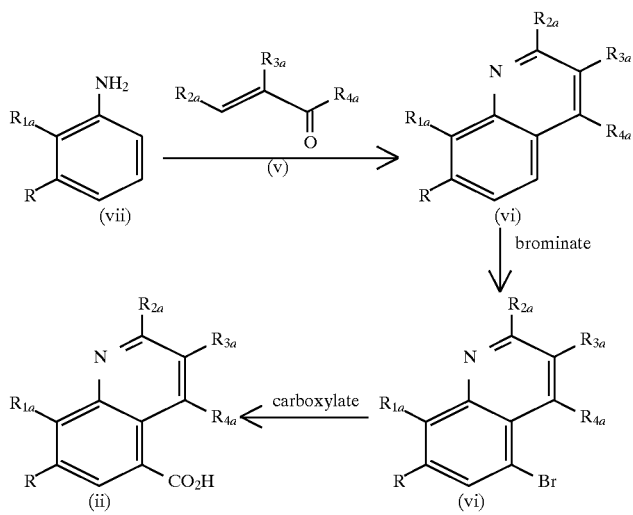

A compound formula (ia) may also be prepared by reaction of a carboxylic acid of formula (ii) with an amine of the formula $H_2NR_{6a}$ (ix), to provide a compound of formula (ia) in which $R_{5a}$ is H, followed by reaction with an appropriate agent of the formula $R_{5a}Y$ (x), wherein $R_{1a}$–$R_{6a}$ are as defined earlier and Y represents a suitable leaving group such as a halogen. The reaction of a carboxylic acid of formula (ii) with an amine of formula (ix) may be carried out under any suitable conditions known to those skilled in the art. Preferably, the carboxylic acid is converted into an acid chloride, mixed anhydride or other activated intermediate prior to reaction with an amine of formula (ix). Preferably, the reaction is carried out in the presence of a suitable base, for example an amine such as triethylamine preferably in an appropriate solvent such as dichloromethane. In some cases a stronger base such as sodium hydride, and a polar solvent such as dimethylformamide, may be required.

Amines of formula (iii) and (ix) and agents of formula (x) are either commercially available, previously described compounds or are prepared using standard procedures known to those skilled in the art. The reaction of a compound of formula (ia) in which $R_5$ is H with an agent of formula (x) may be carried out under any suitable conditions known to those skilled in the art. Preferably, the reaction is carried out using an appropriate base, such as sodium hydride, preferably in an appropriate solvent such as dimethylformamide. Agent (x) can be an alkylating agent such as propyl bromide, an acylating agent such as benzoyl chloride or a sulphonylating agent such as methanesulphonyl chloride.

A compound of formula (i) may also be prepared by interconversion of other compounds of formula (i). For example, a compound in which $R_3$ contains an alkoxy group may be prepared by appropriate alkylation of a compound in which $R_3$ contains a hydroxy group.

Compounds in which $R_2$–$R_4$ contain a CO-alkyl, CO-aryl, CO-heteroaryl, CO-alkylaryl, CO-alkylheteroxyl, CO-alkylheterocyclo may be prepared from compounds in which $R_2$–$R_4$ contain a CN group by addition of a suitable organometallic agent (such as a Grignard reagent).

By way of further example, compounds in which $R_2$–$R_4$ contain an oxime may be prepared from compounds in which $R_2$–$R_4$ contain a carbonyl group. This transformation may be carried out using any appropriate standard conditions known to those skilled in the art. Compounds of formula (i) in which $R_2$–$R_4$ contain a carbonyl group may be reduced using standard conditions known to those skilled in the art (for example with sodium borohydride in an appropriate solvent) to provide compounds in which $R_2$–$R_4$ contains an alcohol group. Compounds in which $R_2$–$R_4$ is alkyl may be prepared by reduction of compounds in which $R_2$–$R_4$ is CO-alkyl using standard conditions known to those skilled in the art (for example hydrazine hydrate in the presence of a suitable base in an appropriate solvent). Other transformations may be carried out on compounds of formula (i) in which $R_2$–$R_4$ contains a carbonyl group. Such transformations include, but are not limited to, reductive amination and alkylation. Any of the above transformations may be carried out either at the end of the synthesis or on an appropriate intermediate.

Compounds of formula (i) in which X is CS may be prepared from compounds of formula (i) in which X is CO using any appropriate conditions known to those skilled in the art, for example by using Lawesson's reagent.

A compound of formula (i) or where appropriate a pharmaceutically-acceptable it thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion tecniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically-acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional an the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, catboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily ester such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 $\mu$m, such as from 0.1 to 50 $\mu$m, preferably less than 10 $\mu$m, for example from 1 to 10 $\mu$m, 1 to 5 $\mu$m or from 2 to 5 $\mu$m. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions nay contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof, are conventional formulations well known in the art, for example, as described in standard text books such as Harry's Cosmeticology published by Leonard Hill Books, Remington's Pharmaceutical Sciences, and the British and U.S. Pharmacopoeias.

Suitably, the compound of formula (i), or if appropriate a pharmaceutically-acceptable salt thereof, will comprise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0,08, 0.1 or 0.2 mg/kg/day, and such therapy may extend for a number of weeks or months.

When used herein the term "pharmaceutically-acceptable" encompasses materials suitable for both human and veterinary use.

The following Examples illustrate the invention

Intermediate 1

8-Methoxyquinoline-5-carboxylic acid

A of 3-amino-4-methoxybenzoic acid (5.0 g), glycerol (4.16 g), and iodine (135 mg) in concentrated sulphuric acid (5 ml) was heated at 180° C. for 2 hours. The reaction was allowed to cool, diluted with water (170 ml), made basic to pH8/9 with 0.88 ammonia and stirred with activated charcoal (2.0 g). The mixture was filtered through Celite and the filtrate acidified to pH4/5 with acetic acid. The precipitate was obtained by filtration and dried in a dessicator to yield the desired product (4.21 g) as a tan solid.

TLC $R_f$ 0.35 (1% Acetic acid, 5% methanol in ethyl acetate).

Intermediate 2

8-Methoxy-2-methylquinoline

A mixture of 8-hydroxyquinaldine (5.0 g) and tetrabutyl ammonium iodide (1.1 g) in tetrahydrofuran (9 ml) was treated at room temperature with sodium hydroxide (4.5 g) in water (45 ml). Methyl iodide (3.7 ml) was added and the reaction stirred overnight. The THF was removed in vacuo and the remaining solution partitioned between ethyl acetate (100 ml) and water (100 ml). The aqueous layer was re-extracted with ethyl acetate and the organic extracts combined. The organic layer was washed with saturated aqueous sodium hydrogen carbonate (100 ml) and saturated aqueous sodium chloride (100 ml). The organic layer was dried over magnesium sulphate, filtered and the filtrate evaporated in vacuo to yield the desired product as an off-white solid (5.85 g).

TLC $R_f$ 0.46 (ethyl acetate).

The following Intermediates were prepared in a similar manner.

Intermediate 3
8-Methoxyquinoline-2-carbonitrile

The title compound was isolated as a white solid (325 mg).

TLC $R_f$ 0.27 (50% ethyl acetate in hexane).

Intermediate 4
2-Bromo-8-methoxyquinoline

Purification by flash chromatography on silica eluting with 50% ethyl acetate in hexane afforded the title compound (1.45 g) as a pale yellow crystalline solid.

TLC $R_f$ 0.55 (50% ethyl acetate in hexane).

Intermediate 5
3-Ethyl-8-methoxyquinoline

Freshly distilled 2-ethyl acrolein (1.7 ml) was added, over 20 minutes, to a solution of o-anisidine (1.5 g) and iodine (20 mg) in 70% sulphuric acid (10 ml) stirring at 110° C. After 2 hours the reaction was cooled to 0° C. and basified with 25% aqueous sodium hydroxide (pH 13). The aqueous layer was extracted with ethyl acetate (2×100 ml) and the extracts combined. The organic layer was extracted with 2M hydrochloric acid (2×100 ml) and the combined acidic extracts basified once again with 25% sodium hydroxide. The aqueous layer was extracted with ethyl acetate (2×100 ml), the extracts combined, dried over magnesium sulphate, filtered, and the filtrate evaporated in vacuo. The residue was purified by column chromatography, eluting with 25%–50% ethyl acetate in hexane, to yield the title product as a tan oil (0.42 g).

TLC $R_f$ 0.17 (50% ethyl acetate in hexane).

Intermediate 6
2-Ethyl-8-methoxyquinoline n-Butyllithium (1 ml, 1.6M in hexanes) was added dropwise to a stirred solution of 8-methoxy-2-methylquinoline (0.25 g) in tetrahydrofuran (4 ml) at −60° C. under an inert atmosphere. The resulting red solution was stirred at −60° C. for 15 minutes, and then warmed to −40° C. Iodomethane (0.27 ml) was then added dropwise and the reaction warmed slowly to room temperature with continued stirring for 12 hours. The reaction was quenched with brine (50 ml) and extracted with dichloromethane (2×5ml). The organic phases were combined, dried over magnesium sulphate and preadsorbed onto silica. Purification was achieved by column chromatography eluting with ethyl acetate to afford the title compound as a pale yellow solid (0.16 g).

TLC $R_f$ 0.53 (ethyl acetate).

Intermediate 7
7-Fluoro-8-methoxyquinoline

A solution of 3-fluoro 2-methoxyaniline (5.0 g) in 1,2-dichlorobenzene (50 ml) was heated to 170° C. and treated with p-toluenesulphonic acid (0.7 g). A solution of acrolein (4.0 g) in 1,2-dichlorobenzeue (20 ml) was added dropwise over 20 minutes. The reaction was stirred for 1 hour at 170° C. before being allowed to cool. The mixture was extracted with 2N hydrochloric acid (3×200 ml) and the combined extracts washed with dichloromethane (20 ml), basified with 25% aqueous sodium hydroxide, and extracted with ethyl acetate (3×200 ml). The combined extracts were dried over magnesium sulphate, filtered and the filtrate evaporated in vacuo. The residue was purified by column chromatography on silica gel eluting with 50% ethyl acetate in hexane to yield the desired product (2.6 g) as a clear oil.

TLC $R_f$ 0.21 (50% ethyl acetate in hexane).

Intermediate 8
5-Bromo-8-methoxy-2-methylquinoline

A solution of 8-methoxy-2-methylquinoline (1.0 g) in methanol (30 ml) was treated at room temperature with bromine (0.31 ml). The mixture was heated at 45° C. for 2 hours and the reaction quenched with 5% aqueous sodium metabisulphite (50 ml). The solution was basified with 25% aqueous sodium hydroxide to pH13 and the product extracted with ethyl acetate (2×100 ml). The extracts were combined, dried over magnesium sulphate, filtered and the filtrate evaporated in vacuo. The residue was dissolved in ethyl acetate and passed through a silica pad. The solution was evaporated in vacuo to yield the desired product as an off-white solid (0.43 g).

TLC $R_f$ 0.57 (ethyl acetate).

The following Intermediates were prepared in a similar manner.

Intermediate 9
5-Bromo-3-ethyl-8-methoxyquinoline

The title compound was isolated as a tan solid (0.50 g).

TLC $R_f$ 0.125 (50% ethyl acetate in hexane).

Intermediate 10
5-Bromo-2-ethyl-8-methoxyquinoline

The title compound was isolated as a brown oily solid (3.3 g),

TLC $R_f$ 0.67 (15% ethyl acetate in dichloromethane).

Intermediate 11
5-Bromo-8-methoxy-2-(trifluoromethyl)quinoline

The title compound (4.15 g) was obtained as a white solid. mp 84°–85° C.

Intermediate 12
5-Bromo-7-fluoro-8-methoxyquinoline

Bromine (0.48 ml) was added dropwise to a solution of 7-fluoro-8-methoxyquinoline (1.6 g) in glacial acetic acid (24 ml). The mixture was heated to 40° C. for 4 h and the reaction quenched with 5% aqueous sodium metabisulphite (100 ml). The solution was basified with 25% aqueous sodium hydroxide to pH13 and the product extracted with ethyl acetate (3×150 ml). The extracts were combined, dried over magnesium sulphate, filtered and the filtrate evaporated in vacuo. The residue was purified by column chromatography on silica gel eluting with 25% ethyl acetate in hexane to yield the desired product as a white solid (0.50 g).

TLC $R_f$ 0.46 (50ethyl acetate in hexane).

Intermediate 13
5Bromo-8-methoxyquinoline-2-carbonitrile

Sodium acetate (690 mg) was added to a solution of Intermediate 3(310 mg) in glacial acetic acid (10 ml). Bromine (0.1 ml) was added dropwise, and the mixture stirred at room temperature for 17 h. It was quenched with 5% aqueous sodium metabisulphite (20 ml), then basified with 25% aqueous sodium hydroxide to pH13 and extracted with ethyl acetate (3×60 ml). The extracts were combined, dried over magnesium sulphate, filtered and the filtrate evaporated in vacuo. The residue was purified by column chromatography on silica gel eluting with 33% ethyl acetate in hexane to yield the desired product as a white solid (365 mg).

TLC $R_f$ 0.63 (50% ethyl acetate in hexane).

Intermediate 14
Methyl-5-bromo-8-methoxyquinoline-2-carboxylate

Purification by flash chromatography gave the title compound (0.48 g) as a white solid.

TLC $R_f$ 0.37 (ethyl acetate in hexane)

Intermediate 15
5-Bromo-8-difluoromethoxyquinoline

Aqueous sodium hydroxide (47%, 15 ml) and benzyltriethylammonium chloride (0.25 g) were added to a suspension of 5-bromo-8-hydroxyquinoline (2.74 g) in dioxane (150 ml). The vigorously stirred mixture was heated to 75° C. and chlorodifluoromethane gas was bubbled through the reaction mixture with a diffuser for 50 minutes. The solution was allowed to cool to room temperature and the reaction mixture was poured into water (250 ml) and extracted with ethyl acetate (3×200 ml). The combined organic extracts were washed with water (2×150ml), dried (magnesium sulphate) and evaporated in vacuo. The residue was purified by column chromatography on silica eluting with 50% ethyl acetate in hexane to furnish the title compound (1.64 g) as a yellow solid.

TLC $R_f$ 0.70 (50% ethyl acetate in hexane).

Intermediate 16
5-Bromo-8-difluoromethoxyquinaldine

Purification by recrystallisation from aqueous methanol afforded the title compound as an offwhite solid (4.8 g).

TLC $R_f$ 0.86 (50% ethyl acetate in hexane).

Intermediate 17
8-Methoxy-2-methylquinoline-5-carboxylic acid

A mixtures of 5-bromo-8-methoxy-2-methylquinoline (2.0 g), triethylamine (11 ml), triphenylphosphine (0.79 g), and bis(tripbenylphosphine)palladium (II) chloride (1.56 g) in tetrahydrofuran (200 ml) and water (90 ml) was stirred in a pressurised reaction vessel and charged with carbon monoxide to a pressure of 160 psi. The vessel was heated to 80° C. and stirred for 72 hours. The reaction was allowed to cool and depressurised. The mixture was filtered ant the organic solvent was removed in vacuo. The aqueous residue was basified with 1M sodium hydroxide and washed with ethyl acetate (300ml). The aqueous solution was acidified to pH 5 with glacial acetic acid and extracted with ethyl acetate (2×400 ml). The organic extracts were combined, dried over magnesium sulphate, filtered and the filtrate evaporated in vacuo to yield the title product (1.0 g) as an off-white solid.

TLC $R_f$ 0.17 (ethyl acetate).

The following Intermediates were prepared in a similar manner:

Intermediate 18
3-Ethyl-8-methoxyquinoline-5-carboxylic acid

The title compound was obtained from 5-bromo-3ethyl-8-methoxyquinoline and isolated as an off-white solid (0.6 g).

TLC $R_f$ 0.7 (10% methanol in ethyl acetate).

Intermediate 19
2-[(t-Butyloxycarbonyl)(methyl)amino]-8-methoxyquinoline-5-carboxylic acid The title compound (0.311 g) was prepared from 5-bromo-2[(t-butyloxycarbonyl)(methyl)amino]-8-methoxyquinoline (1.18 g). Mass spectrum (EI) 233 [M-Boc+H]$^{30}$ The following Intermediates were prepared in a similar manner, but on acidification of the aqueous phase to pH4–5 with glacial acetic acid, the title compounds were precipitated. They were removed by filtration and dried in vacuo.

Intermediate 20
8-Difluoromethoxyquinoline-5-carboxylic acid

The title compound was isolated as a beige solid (0.85 g), mp 280° C. (dec.).

Intermediate 21
8-Difluoromethoxyquinaldine-5-carboxylic acid

The title compound was isolated as a beige solid (2.9 g).

TLC $R_f$ 0.6 (10% methanol in dichloromethane).

Intermediate 22
7-Fluoro-8-methoxyquinoline-5-carboxylic acid

The title compound was isolated as an off-white solid (0.58 g).

TLC $R_f$ 0.1 (ethyl acetate).

Intermediate 23
8-Methoxy-2-(pyrid-3-y)-quinoline-5-carboxylic acid

The title compound was obtained as a beige powder (366 mg).

mp 264° C. (dec.).

The following Intermediates were prepared in a similar manner, but using dimethylformamide as the solvent instead of tetrahydrofuran:

Intermediate 24
2-Cyano-8-methoxyquinoline-5-carboxylic acid

The title compound was isolated as an off-white solid (0.304 g).

TLC $R_f$ 0.1 (ethyl acetate).

Intermediate 25
8-Methoxy-2-(trifluoromethyl)quinoline-5-carboxylic acid

The title compound (3.1 g) was obtained as a white solid. mp 248°–249° C.

Intermediate 26
2-Ethyl-8-methoxyquinoline-5-carboxylic acid

A mixture of 5-bromo-2-ethyl-8-methoxyquinoline (3.3 g), sodium hydroxide (3.1 g, 46% solution in water), triphenylphosphine (0.22 g), and bis(triphenylphosphine) palladium (II) chloride (0.14 g) in tetrahydrofuran (14 ml) and water (7 ml) was stirred in a pressurised reaction vessel and charged with carbon monoxide to a pressure of 160 psi. The vessel was heated to 105° C. and stirred for 24 hours. The reaction was allowed to cool and depressurised. The mixture was filtered and the solid collected washed with tetrahydrofuran (2×10 ml). The solid was dissolved in hot methanol (10 ml) and water (10 ml), and the solution filtered to remove any remaining solids. The hot solution was treated with glacial acetic acid (2 ml) and cooled in ice. The resulting precipitate was filtered off and dried over silica gel under vacuum to afford the title compound as a white solid (0.44 g).

TLC $R_f$ 0.2 (ethyl acetate).

Intermediate 27
3-Methoxyquinoline-5-carbonyl chloride, hydrochloride

A suspension of 8-methoxyquinoline-5-carboxylic acid (1.5 g) in dichloromethane (12 ml) was cooled to 0° C. and treated with oxalyl chloride (1.3 ml) followed by DMF (8 drops). The reaction was allowed to warm to room temperature and stirred overnight. The solvent was removed in vacuo and the residue azeotroped with toluene (2×10 ml) to yield the desired product (1.61 g) as an off-white powder.

The following acid chlorides were prepared in a similar manner from the appropriate carboxylic acid:

Intermediate 28
8-Methoxy-2-methylquinoline-5-carbonyl chloride, hydrochloride The tide compound was isolated as an off-white solid (0.5 g).

Intermediate 29
3-Ethyl-8-methoxyquinoline-5-carbonyl chloride, hydrochloride The title compound was isolated as an off-white solid (0.68 g); Mp 185°–86° C. (dec.).

Intermediate 30
7-Fluoro-8-methoxyquinoline-5-carbonyl chloride, hydrochloride The title compound was isolated as a brown solid (0.64 g).

Intermediate 31
2-Cyano-8-methoxyquinoline-5-carbonyl chloride, hydrochloride The title compound was isolated as a brown solid (0.32 g).

Intermediate 32
8-Difluoromethoxyquinoline-5-carbonyl chloride, hydrochloride The title compound was obtained as a beige solid (853 mg).

Intermediate 33
2-Ethyl-8-methoxyquinoline-5-carbonyl chloride, hydrochloride The title compound was isolated as a deep red oily solid (0.48 g).

Intermediate 34
8-Methoxy-2-(3-pyridyl)-quinoline-5-carbonyl chloride, hydrochloride The title compound was obtained as a beige solid (0.39 g).

Intermediate 35
8-Methoxy-2-(trifluoromethyl)quinoline-5-carbonyl chloride, hydrochloride The tide compound was obtained as a pale yellow solid.

Intermediate 36
4-Amino-3-chloropyridine

A solution of 4-aminopyridine (4.0 g) in concentrated hydrochloric acid (50 ml) was treated at 80°–85° C. with an aqueous solution of hydrogen peroxide (13.5% w/v). The solution was cooled to 0° C. After 30 minutes, the solution was carefully treated with an aqueous sodium hydroxide solution (50%w/v) maintaining the temperature below 15° C. The precipitate was filtered off and air dried to afford the title compound as a white solid (4.9 g).

TLC $R_f$ 0.36 (ethyl acetate).
Mp 65°–67° C.

Intermediate 37
8-Methoxy-2-(3-pyridyl)quinoline

Powdered potassium hydroxide (675 mg) was added to a stirred mixture of 2-bromo-8-methoxyquinoline (956 mg), diethyl(3-pyridyl)borane (590 mg), tetrakis (triphenylphosphine)-palladium(0) (250 mg) and tetra-n-butylammonium iodide (740 mg) in anhydrous tetrahydrofuran (60ml). The stirred mixture was refluxed under an inert atmosphere for 1.25 h. The solvent was removed in vacuo and the residue partitioned between dichloromethane (100 ml) and water (80ml). The aqueous phase was reextracted with dichloromethane (2×50 ml) and the combined organic phases were dried (magnesium sulfate), filtered through a small pad of Celite and evaporated in vacuo. The crude product was purified by flash chromatography on silica, eluting with ethyl acetate to yield the title compound (780 mg) as a clear oil.

TLC $R_f$ 0.25 (ethyl acetate).

Intermediate 38
5-Bromo-8-methoxy-2-(3-pyridyl)quinoline

Bromine (200 μl) was added in a dropwise manner to a stirred and cooled (0°–5° C.) solution of 8-methoxy-2-(3-pyridyl)quinoline (780 mg) in methanol (30 ml) under a nitrogen atmosphere. The reaction mixture was stirred for 15 minutes then quenched by the addition of 5% aqueous sodium metabisulfite solution (7ml). The reaction mixture was evaporated in vacuo and the residue partitioned between 0.5N sodium hydroxide solution (65 ml) and dichloromethane (75 ml). The aqueous phase was reextracted with dichloromethane (2×75 ml) and the combined organic phases were dried (magnesium sulfate), filtered and evaporated in vacuo. Trituration with diethyl ether afforded the title compound (570 mg) as a pale brown solid.

TLC $R_f$ 0.2 (ethyl acetate).

Intermediate 39
5-[8-Methoxy-5-[N-(3,5-dichloropyridin-4-yl)]-aminocarbonylquinolin-2-yl]-2-trimethylstannyl-2H-tetrazole 2-Cyano-8-methoxyquinoline-5-[N-(3,5-dichloropyridin-4-yl)]-carboxamide (390 mg) and trimethyltin azide (480 mg) in toluene (20 ml) and tetrahydrofuran (2 ml) were heated to reflux for 16 hours. The reaction was cooled to room temperature and the resulting precipitate filtered off, washed with toluene (2×5 ml) and dried in vacuo at 40° C. to yield the title compound as a pale yellow solid (299 mg);
Mp 229°–231° C.

Intermediate 40
Methyl 8-hydroxyquinoline-2-carboxylate

8-Hydroxyquinoline-2-carboxylic acid (2.08 g) and tetrahydrofuran (200 ml) were combined and stirred with ice bath cooling. Diazomethane (approx. 16.6 mmol in solution in diethyl ether) was then added and the whole stirred for 1.5 h as it slowly warmed to room temperature. Nitrogen was blown through the reaction mixture to purge any excess diazomethane and the solution was evaporated in vacuo to give the title compound (1.6 g).

TLC $R_f$ 0.12 (50% ethyl acetate in hexane).

Intermediate 41
Methyl 8-methoxyquinoline-2-carboxylate

Methyl 8-hydroxyquinoline-2-carboxylate (1.6 g), acetone (15 ml), potassium carbonate (1.3 g) and iodomethane (0.6 ml) were combined and stirred at room temperature for 48 h. The solvents were removed in vacuo and the resulting white residue suspended in water (25 ml)

which was extracted with ethyl acetate (3×25 ml). The combined organic layers were dried (magnesium sulphate) and the solvents removed in vacuo to give the title compound as a white solid (1.72 g).

TLC $R_f$ 0.22 (50% ethyl acetate in hexane).

Intermediate 42

5-Bromo-8-methoxyquinoline-2-carboxylic acid

Methyl 5-bromo-8-methoxyquinoline-2-carboxylate (1.54 g), tetrahydrofuran (40 ml), water (40 ml) and lithium hydroxide monohydrate (0.436 g) were combined and stirred at room temperature for 1.5 h. The tetrahydrofuran was removed in vacuo and the resulting aqueous mixture was acidified with hydrochloric acid. The resulting white precipitate was collected by filtration and dried in vacuo to give the title compound (1.33 g) as a white solid.

Mass spectrum (EI) 296 & 298 [M+H]$^+$

Intermediate 43

5-Bromo-2-t-butyloxycarbonylamino-8-methoxyquinoline

5-Bromo-8-methoxyquinoline-2-carboxylic acid (2 g), t-butanol (25 ml) and triethylamine (1.48 ml) were combined under a nitrogen atmosphere and heated to 80° C. Diphenylphosphorylazide (2.29 ml) was added to the solution and heating was continued for 60 h by which time a white preciptate was present. The reaction mixture was evaporated in vacuo onto silica and purified by flash chromatography to give the title compound (1.21 g) as an off white solid.

TLC $R_f$ 0.50 (50% ethyl acetate in hexane).

Intermediate 44

5Bromo-2[(t-butyloxycarbonyl)(methyl)amino]-8-methoxyquinoline

5-Bromo-2-t-butyloxycarbonylamino-8-Methoxyquinoline (1.21 g) and tetrahydrofuran (20 ml) were combined at room temperature under a nitrogen atmosphere. Sodium hydride (60% dispersion in oil) (164 mg) was added and the reaction mixture stirred for 2 h whilst effervescence occurred and a yellow colour appeared. Iodomethane (0.43 ml) was then added and stirring was continued for 2 h after which time the reaction was diluted with ethyl acetate (100 ml), washed successively with water, saturated aqueous sodium bicarbonate and brine, then dried (magnesium sulphate) and evaporated in vacuo to give the title compound (1.1 g) as a yellow solid.

TLC $R_f$ 0.60 (50% ethyl acetate in hexane).

Intermediate 45

4-Nitrophenyl 2[(t-butyloxycarbonyl)(methyl)amino]-8-methoxyquinoline-5-carboxylate 2-[(t-Butyloxycarbonyl)(methyl)amino]-8-methoxyquinoline-5-carboxylic acid (0.311 g), ethyldimethylaminopropylcarbodiimide hydrochloride (0.269 g), 4-nitrophenol (0.195 g), N,N-dimethylaminopyridine (20 mg) and dichloromethane (20 ml) were combined and then stirred at room temperature for 17 h. The reaction mixture was evaporated in vacuo onto silica and purified by flash chromatography to give the title compound (0.384 g) as a pale yellow solid.

TLC $R_f$ 0.50 (50% ethyl acetate in hexane).

The following Intermediate was prepared in a similar manner using the appropriate starting materials.

Intermediate 46

4-Nitrophenyl 8-difluoromethoxyquinaldine-5-carboxylate

Purification by column chromatography eluting with 50% ethyl acetate in hexane yielded the title compound as a cream solid (0.63 g).

TLC $R_f$ 0.76 (10% methanol in dichloromethane).

Intermediate 47

8-t-Butyldimethylsilyloxyquinaldine

8-Hydroxyquinaldine (10 g), t-butyldimethylsilyl chloride (10 g) and imidazole (8.6 g) were dissolved in N,N-dimethylformamide (150 ml) and stirred at ambient temperature overnight. Further t-butyldimethylsilyl chloride (4.7 g) was added and the reaction stirred for another 30 minutes. The reaction was diluted with water (600 ml) and extracted with dichloromethane (3×300 ml). The combined organic phases were dried over magnesium sulphate and concentrated in vacuo to afford the title compound as an orange oil (17 g).

TLC $R_f$ 0.9 (10% methanol in ethyl acetate).

Intermediate 48

5-Bromo-8-t-butyldimethylsilyloxyquinaldine

N-bromosuccinimde (14 g) was added in one portion to a stirred solution of 8-t-butyldimethylsilyloxyquinaldine (15 g) in chloroform at −40° C. under an inert atmosphere. The reaction was warmed to room temperature and then heated to reflux for 6 h. Further N-bromosuccinimide (6 g) was added to the reaction at room temperature and stirring continued for 3 days. The reaction mixture was poured into 5% aqueous sodium metabisulphite solution (300 ml) and extracted with chloroform (3×300 ml). The combined organic phases were dried over magnesium sulphate and concentrated in vacuo to afford the title compound as an orange oil (16.4 g).

TLC $R_{f\ b\ 0.8}$ (dichloromethane).

Intermediate 49

5-Bromo-8-hydroxyquinaldine

Tetrabutylammonium fluoride (54 ml, 1M in tetrahydrofuran) was added dropwise to a stirred solution of 5-bromo-8-t-butyldimethylsilyloxyquinaldine (16.3 g) in tetrahydrofuran (500 ml). After stirring for 10 minutes the reaction was diluted with dichloromethane (500 ml) and extracted with water (3×200 ml). The organic phase was dried over magnesium sulphate and concentrated in vacuo. Purification by recrystallisation from aqueous methanol afforded the title compound as an off white solid (7.7 g).

TLC $R_f$ 0.58 (10% methanol in dichloromethane).

EXAMPLE 1

8-Methoxyquinoline-5-[N-pyridin-4-yl)]carboxamide

A suspension of 8-methoxyquinoline-5-carbonyl chloride hydrochloride (0.5 g) in dichloromethane (3 ml) was added to a solution of 4-aminopyridine (94 mg) and triethylamine (140 µl) in dichloromethane (3 ml) at 0° C. under nitrogen. The reaction was stirred at room temperature for 16 hours and then diluted with dichloromethane. The organic solution was washed with saturated aqueous sodium hydrogen carbonate (20 ml), water (5 ml) and the aqueous layer extracted with dichloromethane (25 ml). The organic extracts were combined and dried over magnesium sulphate, filtered and the filtrate evaporated in vacuo. The residue was purified by column chromatography on silica gel eluting with 15% methanol in dichloromethane to yield the title compound as an off-white solid (130 mg).

TLC $R_f$ 0.4 (15% methanol in dichloromethane); Mp 257°–258° C.

The following Examples were prepared from 8-methoxyquinoline-5-carbonyl chloride, hydrochloride and the appropriate amine using a similar procedure to the one described above.

EXAMPLE 2
8-Methoxyquinoline-5-[N-(thiazol-2-yl)]carboxamide

The title compound was obtained as an off-white solid (80 mg).

TLC $R_f$ 0.3(10% methanol in ethyl acetate); Mp 249°–251° C.

EXAMPLE 3
8-Methoxyquinoline-5-[N-(2-trifluoromethoxyphenyl)]carboxamide

The title compound was obtained as an off-white solid (125 mg).

TLC $R_f$ 0.54 (10% methanol in ethyl acetate); Mp 206°–208° C.

EXAMPLE 4
8Methoxyquinoline-5[N-2-(piperidin-1-yl)phenyl]carboxamide

The title compound was obtained as an off-white solid (100 mg).

TLC $R_f$ 0.50 (10% methanol in dichloromethane); Mp 214°–216° C.

EXAMPLE b 5
8-Methoxyquinoline-5-[N-(2-fluorophenyl)]carboxamide

The title compound was obtained as an off-white solid (90 mg).

TLC $R_f$ 0.41 (10% methanol in ethyl acetate); Mp 190°–192° C.

EXAMPLE 6
8-Methoxyquinoline-5-[N-(2-methylphenyl)]carboxamide

The title compound was obtained as an o-white solid (630 mg).

TLC $R_f$ 0.46 (10% methanol in dichloromethane); Mp 215°–216° C.

EXAMPLE 7
8-Methoxyquinoline-5-[N-(2,6-dimethylphenyl)]carboxamide

The title compound was obtained as an off-white solid (550 mg).

TLC $R_f$ 0.43 (10% methanol in dichloromethane); Mp 273°–275° C.

EXAMPLE 8
8-Methoxyquinoline-5-[N-(2-chlorophenyl)]carboxamide

The title compound was obtained as an off-white solid (490 mg)

TLC $R_f$ 0.47 (5% methanol in dichloromethane); Mp 196°–197° C.

EXAMPLE 9
8-Methoxyquinoline-5-[N-(2-methoxyphenyl)]carboxamide

The tide compound was obtained as an off-white solid (150 mg).

TLC $R_f$ 0.60 (10% methanol in dichloromethane).

EXAMPLE 10
8-Methoxyquinoline-5-[N-(4-methoxyphenyl)]carboxamide

The title compound was obtained as an off-white solid (780 mg). Mass spectrum (EI) 309 [M+H]$^+$

EXAMPLE 11
8-Methoxyquinoline-5-[N-(2-chloro-6-methylphenyl)]carboxamide

The title compound was obtained as a off-white solid (700 mg). Mass spectrum (EI) 327 [M+H]$^+$ The following Example was prepared from 8-methoxy-2-methylquinoline-5-carbonyl chloride hydrochloride and 2-chloroaniline using a procedure similar to that described above.

EXAMPLE 12
8-Methoxy-2-methylquinoline-5-[N-(2-chlorophenyl)]carboxamide

Purification by flash chromatography on silica eluting with 50% ethyl acetate in dichloromethane afforded the title compound (50 mg) as a pale brown solid.

TLC $R_f$ 0.4 (50% ethyl acetate in dichloromethane); Mp 225°–226° C.

EXAMPLE 13
8-Methoxyquinoline-5-[N-(2, 5-dichloropyridin-3yl)]carboxamide

A solution of 3-amino-2,5-dichloropyridin (504 mg) in anhydrous DMF (5 ml) was carefully added to a suspension of sodium hydride (272 mg, 60% dispersion in oil) in anhydrous DMF (5 ml) at room temperature under nitrogen. The resultant mixture was stirred for 10 minutes and then treated dropwise with a solution of 8-methoxyquinoline-5-carbonyl chloride hydrochloride (800 mg) in anhydrous DMF (10 ml). The reaction was stirred for two hours at 50° C. and 18 hours at room temperature. The solvent was evaporated in vacuo and the residue partitioned between dichloromethane (50 ml) and saturated aqueous sodium hydrogen carbonate solution (50 ml). The aqueous layer was extracted with dichloromethane (30 ml). The organic extracts were combined and washed with saturated aqueous sodium chloride (10 ml), dried over magnesium sulphate, filtered and the filtrate evaporated in vacuo. The residue was purified by column chromatography on silica gel eluting with 10% methanol in ethyl acetate to yield the title compound as an off-white solid (230 mg).

TLC $_f$ 0.30 (10% methanol in ethyl acetate); Mp 251–252° C.

The following Examples were prepared from 8-methoxyquinoline-5-carbonyl chloride, hydrochloride and the appropriate amine using a similar procedure to the one described above.

EXAMPLE 14
8-Methoxyquinoline-5-[(pyrimidin-4-yl)]carboxamide

The title compound was obtained as an off-white solid (130 mg).

TLC $R_f$ 0.39 (15% methanol in ethyl acetate); Mp 225°–226° C.

EXAMPLE 15
8-Methoxyquinoline-5-[N-(3,5-dichloropyridin-2-yl)]carboxamide

The title compound was obtained as an off-white solid (89 mg).

EXAMPLE 16
8-Methoxyquinoline-5-[N-(3,5-dichloropyridin-4-yl)]carboxamide

The title compound was obtained as an off-white solid (452 mg).

TLC $R_f$ 0.45 (10% methanol in dichloromethane); Mp 258°–260° C.

EXAMPLE 17
8-Methoxyquinoline-5-[N-(4,6-dichloropyrimidin-5-yl)]carboxamide

The title compound was obtained as an off-white solid (264 mg).

TLC $R_f$ 0.39 (10% methanol in ethyl acetate); Mp 249°–251° C.

EXAMPLE 18
8-Methoxyquinoline-5-[N-(4-chloropyridin)-4-yl)]carboxamide

The title compound was obtained as an off-white solid (40 mg).

TLC $R_f$ 0.35 (10% methanol in dichloromethane); Mp 232°–234° C.

EXAMPLE 19
8-Methoxyquinoline-5-[N-(2-trifluoromethylphenyl)]carboxamide

The title compound was obtained as an off-white solid (470 mg).

TLC $R_f$ 0.50 (15% methanol in ethyl acetate); Mp 247°–248° C.

EXAMPLE 20
8-Methoxyquinoline-5-[N-(3-bromo-5-methylpyridin-2-yl]carboxamide The title compound was obtained as an off-white solid (250 mg)

TLC $R_f$ 0.15 (3% methanol in dichloromethane).

EXAMPLE 21
8-Methoxyquinoline-5-[N-(2-chloropyridin-3-yl)]carboxamide

The title compound was obtained as an off-white solid (60 mg).

TLC $R_f$ 0.15 (3% methanol in ethyl acetate).

The following Examples were prepared from 8-methoxy-2-methylquinoline-5-carbonyl chloride hydrochloride and the appropriate amine using a procedure similar to that described above.

EXAMPLE 22
8-Methoxy-2-methylquinoline-5-[N-(3-chloropyridin-4-yl)]carboxamide Purification by flash chromatography on silica eluting with 10% methanol in ethyl acetate furnished the title compound (190 mg) as a pale yellow solid.

TLC $R_f$ 0.35 (10% methanol in ethyl acetate); Mp 222°–223.5° C.

EXAMPLE 23
8Methoxy-2-methylquinoline-5-[N-(5-chloropyrimidin-4yl)]-carboxamide Purification by flash chromatography on silica eluting with 10% methanol in ethyl acetate and trituration with diethyl ether afforded the title compound (110 mg) as a pale yellow solid.

TLC $R_f$ 0.38 (10% methanol in ethyl acetate); Mp 192°–193.5° C.

EXAMPLE 24
8-Methoxy-2-methylquinoline-5-[N-(3,5-dichloropyridin-4-yl)]carboxamide The title compound was obtained as an off-white solid (20 mg).

TLC $R_f$ 0.58 (5% methanol in ethyl acetate); Mp 273°–275° C. (dec.).

The following Examples were prepared from the appropriate quinoline carbonyl chloride hydrochloride and 4-amino-3,5-dichloropyridin using a procedure similar to that described in Example 13.

EXAMPLE 25
3-Ethyl-8-methoxyquinoline-5-[N-(3,5dichloropyridin-4-yl)]-carboxamide The title compound was obtained as an off-white solid (50 mg).

TLC $R_f$ 0.34 (5% methanol in dichloromethane); Mass spectrum (EI) 376 [M+H]$^+$

EXAMPLE 26
7-Fluoro-8-methoxyquinoline-5-[N-(3,5-dichloropyridin-4-yl)]carboxamide The title compound was obtained as an off-white solid (210 mg).

TLC $R_f$ 0.48 (ethyl acetate); Mass spectrum (EI) 366 [M+H]$^+$

EXAMPLE 27
2-Cyano-8-methoxyquinoline-5-[N-(3,5-dichloropyridin-4-yl)]-carboxamide The title compound was obtained as an off-white solid (72 mg).

TLC $R_f$ 0.48 (ethyl acetate); Mass spectrum (EI) 373 [M+H]$^+$

EXAMPLE 28
2-Ethyl-8-methoxyquinoline-5-[N-(3, 5-dichloropyridin-4-yl)carboxamide Purification was achieved by column chromatography eluting with ethyl acetate to afford the title compound as a peach solid (0.14 g).

TLC $R_f$ 0.35 (ethyl acetate); Mp 256.5°–257.5° C.

EXAMPLE 29
8-Difluoromethoxyquinoline-5-[N-(3, 5-dichloropyridin-4-yl]carboxamide The title compound was obtained as a white solid (530 mg).

TLC $R_f$ 0.25 (50% ethyl acetate in hexane); Mp 200°–202° C.

EXAMPLE 30
8-Methoxy-2-(3-pyridyl)quinoline-5-[N-(3,5-dichloropyridin-4-yl)]carboxamide Purification by flash chromatography on silica, eluting with 10% methanol in ethyl acetate yielded the title compound (175 mg) as a white powder.

TLC $R_f$ 0.4 (10% methanol in ethyl acetate); Mp 258°–259° C.

EXAMPLE 31
8-Methoxy-2(trifluoromethyl)quinoline-5-[N-(3,5-dichloropyridin-4-yl)]carboxamide The title compound (0.94 g) was obtained as a white solid. Mp 254°–255° C.; TLC $R_f$ 0.24 (50% ethyl acetate in hexane).

EXAMPLE 32
8-Hydroxyquinoline-5-[N-(3,5-dichloropyridin-4yl)]carboxamide

Sodium hydride (1.6 g, 60% dispersion in oil) was washed with diethyl ether under nitrogen and dried in vacuo. Anhydrous N,N-dimethylformamide (20 ml) was added followed by the careful addition of a solution of ethanethiol (3ml) in DMF (3ml). A solution of 8methoxyquinoline-5-[N-(3, 5dichloropyridin-4-yl)]carboxamide (100 mg) in DMF (5 ml) was added to the mixture and the reaction refluxed for 1.5 hours. The solvent was removed in vacuo and the residue partitioned between saturated aqueous ammonium chloride solution (50 ml) and dichloromethane (50 ml). The aqueous phase was re-extracted with dichloromethane (75 ml) and the organic extracts combined. The organic phase was dried over magnesium sulphate, filtered, and the filtrate evaporated in vacuo. The residue was partitioned between dichloromethane (20 ml) and 0.5M aqueous sodium hydroxide solution. The aqueous phase was separated and acidified to pH 4/5 with glacial acetic acid. The preciptate was collected by filtration and dried in vacuo to yield the title compound as an off-white solid (20 mg).

Mass spectrum (EI) 334 [M]+

EXAMPLE 33
8-Methoxyquinoline-5-[N-(3,5dichloropyridin-4-yl)]carboxamide, dihydrochloride A solution of 8-methoxyquinoline-5-[N-3,5-dichloropyridin-4-yl)]carboxamide (114 mg) in methanol (50 ml) was treated with hydrogen chloride gas for 5 minutes at 25° C. The solution was evaporated in vacuo to yield the title compound as an off-white solid (138 mg).

Elemental Analysis

Calculated 45.64% C 3.11% H 9.98% N; Observed 44.51% C 3.09% H 9.67% N

EXAMPLE 34
8-Methoxyquinoline-5-[N-(3,5-dichloropyridin-4-yl)]carboxamide, dihydrobromide Cooled methanol (50 ml) was carefully treated with acetyl bromide (0.25 ml) and the mixture stirred at below 5° C. for 30 minutes. The solution was allowed to warm to room temperature and 8-methoxyquinoline-5-[N-(3,5-dichloropyridin-4-yl)]carboxamide (105 mg) was added. After 30 minutes the solution was evaporated in vacuo to yield the title compound as an off-white solid (148 mg),

EXAMPLE 35
5-[8-Methoxy-5-[N-(3,5-dichloropyridin-4-yl)]aminocarbonylquinolin-2-yl]-2H-tetrazole dihydrochloride salt Hydrogen chloride (0.6 ml, 1M in diethyl ether) was added to a stirred suspension of 5-[8-methoxy-5-[N-(3,5-dichloropyridin-4-yl)]-aminocarbonylquinolin-2-yl ]-2-trimethylstannyl-2H-tetrazole (150 mg) in tetrahydrofuran (10 ml) at room temperature under an inert atmosphere with immediate dissolution being observed. The reaction was stirred at room temperature for 90 minutes and the resulting precipitate filtered off, washed with diethyl ether and dried in vacuo at 40° C. to afford the title compound as a white solid (92 mg).

Mp 242°–244° C.; Mass spectrum (EI) 416 [M+H]+free base

EXAMPLE 36
5-[8-Methoxy-5-[N-(3,5-dichloropyridin-4-yl)]-aminocarbonylquinolin-2-yl]-2-methyltetrazole and 5-[8-Methoxy-5-[N-(3,5-dichloropyridin-4yl)]-aminocarbonylquinolin-2-yl]-1-methyltetrazole 5-[8-Methoxy-5-[N-(3,5dichloropyridin-4-yl)]-aminocarbonylquinolin-2-yl]-2-trimethylstannyl-2H-tetrazole (153 mg) and iodomethane (1.0 ml) were dissolved in methanol (2.5 ml) and stirred under an inert atmosphere at room temperature for 5 days. The solvent was removed in vacuo and the resulting solid suspended in diethyl ether, filtered and washed with diethyl ether (3×10 ml). Purification by column chromatography eluting with 5% methanol in dichloromethane afforded a 7:1 mixture of the title compounds respectively as a white solid (55 mg).

TLC $R_f$ 0.71 (10% methanol in dichloromethane); Mp 273°–275° C.

EXAMPLE 37
2-Acetyl-8-methoxyquinoline-5-[N-(3,5dichloropyridin-4-yl)]carboxamide Methyl magnesium bromide (0.6 ml, 3.0M in diethyl ether) was added dropwise to a stirred solution of 2-cyano-8-methoxyquinoline-5-[N-(3,5-dichloropyridin-4-yl)]carboxamide (300 mg) in tetrahydrofuran (20 ml) at room temperature under an inert atmosphere. The reaction was stirred at room temperature for 1 hour then poured into brine (25 ml) and extracted with ethyl acetate (4×25 ml). The combined organic phases were dried over magnesium sulphate and concentrated in vacuo. Purification by column chromatography eluting with 5% methanol in dichloromethane afforded the title compound as a pale yellow solid (180 mg).

TLC $R_f$ 0.42 (ethyl acetate); Mp 257°–259° C.

EXAMPLE 38
2-(1-Methoxyiminoethyl)-8-methoxyquinoline-5-[N-(3,5-dichloropyridin-4-yl)]carboxamide 2-Acetyl-8-methoxyquinoline-5-[N-(3,5-dichloropyridin-4-yl)]carboxamide (100 mg), methoxylamine hydrochloride (75 mg) and pyridine (0.12 ml) in toluene (50 ml) were heated to reflux under Dean-Stark conditions for 3 days. The cooled reaction mixture was evaporated to dryness in vacuo and passed through a silica column eluting with 66% ethyl acetate in hexane to afford the title compound as a white solid (20 mg).

TLC $R_f$ 0.29 (66% ethyl acetate in hexane); Mp 273°–275° C.

EXAMPLE 39
2-(1-Hydroxyethyl)-8-methoxyquinoline-5-[N-(3,5-dichloropyridin-4-yl)]carboxamide Sodium borohydride (50 mg) was added to a stirred solution of 2-acetyl-8-methoxyquinoline-5-[N-( 3,5-dichloropyridin-4-yl)]carboxamide (180 mg) in methanol (10 ml) at ambient temperature. The reaction was stirred for 90 minutes, quenched with water (dropwise) and the methanol removed in vacuo. The residue was partitioned between ethyl acetate (4×20 ml) and water (10 ml). The combined organic phases were dried over magnesium sulphate and concentrated in vacuo. Purification by column chromatography eluting with 4% methanol in dichloromethane yielded the title compound as an orange solid (68 mg).

TLC $R_f$ 0.28(10% methanol in dichloromethane); Mp 252°–254° C.

EXAMPLE 40
2-[(t-Butyloxycarbonyl)-(methyl)amino-8-methoxyquinoline-5-[N-(3,5-dichloropyrid-4-yl)]carboxamide 4-Amino-3,5-dichloropyridin (138 mg) and dimethylformamide (10 ml) were combined under a nitrogen atmosphere at room temperature. Sodium hydride (60% dispersion in oil) (51 mg) was added and stirring was continued for 3h. 4-Nitrophenyl 2-[(t-butyloxycarbonyl) (methyl)amino]-8-methoxyquinoline-5-carboxylate (384 mg) was then added as a solution in dimethylformamide (10 ml) and stirring was continued for 16h. The reaction mixture was evaporated in vacuo onto silica and purified by flash chromatography to give the title compound (217 mg) as a white solid.

TLC $R_f$ 0.20 (50% ethyl acetate in hexane); Mp 184°–186° C.

The following Example was prepared in a similar manner using the appropriate starting materials.

EXAMPLE 41
8-Difluoromethoxyquinaldine-5-[N-3,5dichloropyidin-4-yl)]carboxamide Purification by column chromatography eluting with 5% methanol in dichloromethane and trituration with ethyl acetate afforded the title compound as a white solid (0.3 g), TLC R$_f$ 0.24 (5% methanol in dichloromethane); Mp 210°–212° C.

EXAMPLE 42

2-(N-Methyl)amino-8-methoxyquinoline-5-[N-(3,5-dichloropyrid-4-yl)]carboxamide 2-[(t-Butyloxycarbonyl)(methyl)(amino]-8-methoxyquinoline-5-[N-(3,5-dichloropyrid-4-yl) ]carboxamide (195 mg), dichloromethane (10 ml) and trifluoroacetic acid (6 ml) were combined and stirred at room temperature for 5 h. The solvents were removed in vacuo and the residue partitioned between dichloromethane and saturated aqueous sodium bicarbonate solution. Extraction was carried out with dichloromethane (3×20 ml) which was then evaporated in vacuo onto silica and purified by flash chromatography to give the title compound (108 mg) as a white solid.

TLC R$_f$ 0.30 (2% ammonium hydroxide in ethyl acetate); Mp 271°–272° C.

EXAMPLE 43

2-[(Pyridin-2-yl)carbonyl]-8-methoxyquinoline-5-[N-(3,5-dichloropyridin-4yl)]carboxamide n-Butyllithium (0.87 ml, 1.6M in hexanes) was added dropwise to a stirred solution of 2-bromopyridine (0.11 ml) in tetrahydrofuran (2 ml) at +78° C. under an inert atmosphere. After stirring at this temperature for 45 minutes, 2-cyano-8-methoxyquinoline-5-[N-(3,5-dichloropyridin-4-yl) ]carboxamide (0.2 g) in tetrahydrofuran (10 ml) was added dropwise and the reaction allowed to warm to room temperature. After stirring at room temperature for 1 hour the reaction was concentrated in vacuo. The residue was partitioned between water (45 ml) and dichloromethane (3×45 ml). The combined organic phases were dried over magnesium sulphate and concentrated in vacuo. Purification by column chromatography eluting with 0. 5% triethylamine and 4.5% methanol in dichloromethane afforded the title compound as a pale orange solid(0.54 mg).

TLC R$_f$ 0.23 (0.5% triethylamine/4.5% methanol in dichloromethane); Mp 185°–187° C.

Assay methods

The assays used to confirm the phosphodiesterase IV inhibitory activity of compounds of formula (i) are standard assay procedures as disclosed by Schilling et al, Anal. Biochem. 216:154 (1994), Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be useful in treating phosphodiesterase IV-related disease states in those assays.

The ability of compounds of formula (i) to inhibit TNF production in human peripheral blood mononuclear cells (PMBC's) is measured as follows. PMBC's are prepared from freshly taken blood or "Buffy coats" by standard procedures. Cells are plated out in RPMI1640+1% foetal calf serum in the presence and absence of inhibitors. LPS (100 ng/ml) is added and cultures are incubated for 22 h at 37° C. in an atmosphere of 95% air/5% $CO_2$. Supernatants are tested for TNFα by ELISA using commercially available kits.

In vivo activity in a skin eosinophilia model is determined by using the methods described by Hellewell et al, Br. J. Pharmacol. 111:811 (1994) and Br. J. Pharmacol. 110:416 (1993). Activity in a lung model is measured using the procedures described by Kallos and Kallos, Int. Archs. Allergy Appl. lmmunol. 73:77 (1984), and Sanjar et al, Br. J. Pharmacol. 99:679 (1990).

An additional lung model, which allows measurement of inhibition of the early and late-phase asthmatic responses and also the inhibition of airway hyperreactivity, is described by Broadley et al, Pulmonary Pharmacol. 7:311 (1994), J. Immunological Methods 190:51 (1996) and British J. Pharmacol. 116:2351 (1995). Compounds of the invention show activity in this model Abbreviations

| LPS | Lipopolysaccharide (endotoxin) |
| ELISA | Enzyme linked immunosorbent assay |

We claim:
1. A compound of the formula (i)

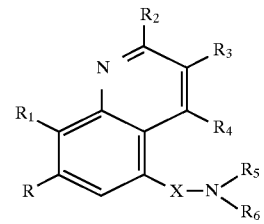

wherein

X is CO or CS;

R is selected from the group consisting of H, halogen, and alkyl;

$R_1$ is selected from the group consisting of OH, alkoxy optionally substituted with one or more halogens, and thioalkyl;

$R_2$, $R_3$, and $R_4$ are the same or different and are each selected from the group consisting of H, $R_7$, $OR_{11}$, $COR_7$, $C(=NOR_7)R_7$, alkyl-$C(=NOR_7)R_7$, halogen, $CF_3$, alkyl-$C(=NOH)R_7$, $C(=NOH)R_7CN$, $CO_2H$, $CO_2 R_{11}$, $CONH_2$, $CONHR_7$, $CON(R_7)_2$, $NR_9R_{10}$, and $CONR_{12}R_{13}$ where $NR_{12}R_{13}$ is a heterocyclic ring optionally substituted with one or more $R_{15}$;

$R_5$ is selected from the group consisting of H, arylalkyl, heteroarylalkyl, heterocycloalkyl, $S(O)_m R_{11}$, and alkyl optionally substituted with one or more substituents selected from the group consisting of hydroxy, alkoxy, $CO_2R_8$, $SO_2NR_{12}R_{13}$, $CONR_{12}R_{13}$, CN, carbonyl oxygen, $NR_9R_{10}$, $COR_{11}$, and $S(O)_n R_{11}$;

$R_6$ is selected from the group consisting of aryl, heteroaryl, heterocyclo, heteroarylalkyl, and heterocycloalkyl;

in $R_5$ and/or $R_6$ the aryl/heteroaryl/heterocyclo portion is optionally substituted with one or more substituents alkyl-$R_{14}$ or $R_{14}$;

$R_7$ represents $R_{11}$ optionally substituted at any position with one or more $R_{16}$;

$R_8$ is selected from the group consisting of H, alkyl, cycloalkyl, arylalkyl, heteroarylalkyl, and heterocycloalkyl;

$R_9$ is selected from the group consisting H, aryl, heteroaryl, heterocyclo, alkyl, cycloalkyl, arylalkyl, heteroarylalkyl, heterocycloalkyl, alkylcarbonyl, alkoxycarbonyl, arylsulphonyl, heteroarylsulphonyl, heterocyclosulphonyl, arylcarbonyl, heteroarylcarbonyl, heterocyclocarbonyl, and alkylsulphonyl;

$R_{10}$ is selected from the group consisting of H, aryl, heteroaryl, heterocyclo, alkyl, cycloalkyl, arylalkyl, heteroarylalkyl, and heterocycloalkyl;

$R_{11}$ is selected from the group consisting of alkyl, cycloalkyl, aryl, heteroaryl, heterocyclo, arylalkyl, heteroarylalkyl, and heterocycloalkyl;

$R_{12}$ and $R_{13}$ are the same or different and are each selected from the group consisting of H and $R_{11}$, or $NR_{12}R_{13}$ represents a heterocyclic ring as defined above;

$R_{14}$ is selected from the group consisting of alkyl (optionally substituted by one or more halogens), cycloalkyl, aryl, heteroaryl, heterocyclo, hydroxy, alkoxy, thioalkyl, aryloxy, heteroaryloxy, heterocyclooxy, arylalkyloxy, heteroarylalkyloxy, heterocycloalkyloxy, $CO_2R_8$, $CONR_{12}R_{13}$, $SO_2NR_{12}R_{13}$, halogen, —CN, —$NR_9R_{10}$, $COR_{11}$, $S(O)_nR_{11}$, and carbonyl oxygen;

$R_{15}$ is selected from the group consisting of alkyl, arylalkyl, and heteroarylalkyl;

$R_{16}$ is selected from the group consisting of alkyl, OH, $OR_{11}$, $NR_9R_{10}$, CN, $CO_2H$, $CO_2R_{11}$, $CONR_{12}R_{13}$, and $COR_{11}$;

m is an integer of up to 2; and n=0–2;

or a pharmaceutically acceptable salt thereof.

2. The compound, according to claim 1, wherein R is H or halogen.

3. The compound, according to claim 1, wherein $R_1$ is alkoxy optionally substituted with one or more halogens.

4. The compound, according to claim 1, wherein $R_2$, $R_3$, and $R_4$ are the same or different and are each selected from the group consisting of H, $CF_3$, $COR_7$, C(=$NOR_7$)$R_7$, C(=NOH)$R_7$, CN, $R_7$, alkyl-C(=NOH)$_7$, and alkyl-C(=$NOR_7$)$R_7$.

5. The compound, according to claim 1, wherein $R_5$ is H or alkyl.

6. The compound, according to claim 1, wherein $R_6$ is aryl or heteroaryl in which the aryl and heteroaryl portions may be optionally substituted with one or more substituents alkyl-$R_{14}$ or $R_{14}$.

7. The compound, according to claim 1, wherein:

R is H;

$R_1$ is optionally-substituted alkoxy;

$R_2$, $R_3$, and $R_4$ are independently selected from the group consisting of H, $R_7$, and alkyl-$R_7$;

$R_7$ is selected from the group consisting of H, OH, alkoxy, aryloxy, heteroaryloxy, heterocyclooxy, arylalkoxy, heteroarylalkoxy, heterocycloalkoxy, alkylamino, $CF_3$, and $R_{11}$;

$R_8$ is selected from the group consisting of H, alkyl, arylalkyl, heteroarylalkyl, and heterocycloalkyl;

$R_9$ is not cycloalkyl;

$R_{10}$ is not cycloalkyl;

$R_{11}$ is not cycloalkyl; and $R_{14}$ is not alkyl, substituted alkoxy, thioalkyl, or cycloalkyl.

8. The compound, according to claim 1, which is 8-methoxyquinoline-5-(N-pyridin-4-yl)carboxamide.

9. The compound, according to claim 1, which is selected from the group consisting of 8-methoxyquinoline-5-[N-(thiazol-2-yl)]carboxamide;

8-methoxyquinoline-5-[N-(2-trifluoromethoxyphenyl)] carboxamide;

8-methoxyquinoline-5-[N-2-(piperidin-1-yl)phenyl] carboxamide;

8-methoxyquinoline-5-[N-(2-fluorophenyl)] carboxamide;

8-methoxyquinoline-5-[N-(2-methylphenyl)] carboxamide;

8-methoxyquinoline-5-[N-(2,6-dimethylphenyl)] carboxamide;

8-methoxyquinoline-5-[N-(2-chlorophenyl)] carboxamide;

8-methoxyquinoline-5-[N-(2-methoxyphenyl)] carboxamide;

8-methoxyquinoline-5-[N-(4-methoxyphenyl)] carboxamide;

8-methoxyquinoline-5-[N-(2-chloro-6-methylphenyl)] carboxamide;

8-methoxy-2-methylquinoline-5-[N-(2-chlorophenyl)] carboxamide;

8-methoxyquinoline-5-[N-(2,5-dichlorophyridin-3-yl)] carboxamide;

8-methoxyquinoline-5-[N-(pyrimidin-4-yl)]carboxamide;

8-methoxyquinoline-5-[N-(3,5-dichloropyridin-2-yl)] carboxamide;

8-methoxyquinoline-5-[N-(3,5-dichloropyridin-4-yl)] carboxamide;

8-methoxyquinoline-5-[N-(4,6-dichloropyrimidin-5-yl)] carboxamide;

8-methoxyquinoline-5-[N-(4-chloropyridin-4-yl)] carboxamide;

8-methoxyquinoline-5-[N-(2-trifluoromethylphenyl)] carboxamide;

8-methoxyquinoline-5-[N-(3-bromo-5-methylpyridin-2-yl)]carboxamide;

8-methoxyquinoline-5-[N-(2-chloropyridin-3-yl)] carboxamide;

8-methoxy-2-methylquinoline-5-[N-(3-chloropyridin-4-yl)]carboxamide;

8-methoxy-2-methylquinoline-5-[N-(5-chloropyrimidin-4-yl)]carboxamide;

8-methoxy-2-methylquinoline-5-[N-(3,5-dichloropyridin-4-yl)]carboxamide;

3-ethyl-8-methoxyquinoline-5-[N-(3,5-dichloropyridin-4-yl)]carboxamide;

7-fluoro-8-methoxyquinoline-5-[N-(3,5-dichloropyridin-4-yl)]carboxamide;

2-cyano-8-methoxyquinoline-5-[N-(3,5-dichloropyridin-4-yl)]carboxamide;

2-ethyl-8-methoxyquinoline-5-[N-(3,5-dichloropyridin-4-yl)]carboxamide;

8-difluoromethoxyquinoline-5-[N-(3,5-dichloropyridin-4-yl)]carboxamide;

8-methoxy-2-(3-pyridyl)quinoline-5-[N-3,5-dichloropyridin-4-yl)]carboxamide;

8-methoxy-2-(trifluoromethyl)quinoline-5-[N-(3,5-dichloropyridin-4-yl)]carboxamide;

8-hydroxyquinoline-5-[N-(3,5-dichloropyridin-4-yl)] carboxamide;

8-methoxyquinoline-5-[N-(3,5-dichloropyridin-4-yl)] carboxamide, dihydrochloride;

8-methoxyquinoline-5-[N-(3,5-dichloropyridin-4-yl)] carboxamide, dihydrobromide;

5-[8-methoxy-5-[N-(3,5-dichloropyridin-4-yl)]-aminocarbonylquinolin-2-yl]-2H-tetrazole dihydrochloride salt;

5-[8-methoxy-5-[N-(3,5-dichloropyridin-4-yl)]-aminocarbonyl-quinolin-2-yl]-2-methyltetrazole;

5-[8-methoxy-5-[N-(3,5-dichloropyridin-4-yl)]-aminocarbonyl-quinolin-2-yl-1-methyltetrazole;

2-acetyl-8-methoxyquinoline-5-[N-(3,5-dichloropyridin-4-yl)]carboxamide;

2-(1-methoxyiminoethyl-8-methoxyquinoline-5-[N-(3,5-dichloropyridin-4-yl)]carboxamide;

2-(1-hydroxyethyl)-8-methoxyquinoline-5-[N-(3,5-dichloropyridin-4-yl)]carboxamide;

2-[(t-butyloxycarbonyl)-(methyl)amino]-8-methoxyquinoline-5-[N-(3,5-dichloropyridin-4-yl)]carboxamide;

8-difluoromethoxyquinaidine-5-[N-(3,5-dichloropyridin-4-yl)]carboxamide;

2-(N-methyl)amino-8-methoxyquinoline-5-[N-(3,5-dichloropyridin-4-yl)]carboxamide; and 2-[(pyridin-2-yl)carbonyl]-8-methoxyquinoline-5-[N-(3,5-dichloropyridin-4-yl)]carboxamide.

10. The compound, according to claim 1, which is in the form of an enantiomer or mixture of enantiomers.

11. A pharmaceutical composition for therapeutic use comprising a compound of claim 1 and a pharmaceutically-acceptable carrier or excipient.

12. A method for treating a disease state capable of being modulated by inhibition of phosphodiesterase IV or Tumour Necrosis Factor, wherein said method comprises administering an effecive amount of a compound of claim 1.

13. The method, according to claim 12, wherein said disease state is a pathological condition associated with the function of phosphodiesterase IV, eosinophil accumulation, or a function of the eosinophil.

14. The method, according to claim 13, wherein said pathological condition is selected from the group consisting of asthma, chronic bronchitis, chronic obstructive airways disease, atopic dermatitis, urticaria, allergic rhinitis, allergic conjunctivitis, vernal conjunctivitis, inflammation of the eye, allergic responses in the eye, eosinophilic granuloma, psoriasis, rheumatoid arthritis, gouty arthritis and other arthritic conditions, ulcerative colitis, Crohn's disease, adult respiratory distress syndrome, diabetes insipidus, keratosis, atopic eczema, atopic dermatitis, cerebral senility, multi-infarct dementia, senile dementia, memory impairment associated with Parkinson's disease, depression, cardiac arrest, stroke, and intermittent claudication.

15. The method, according to claim 13, wherein said pathological condition is selected from the group consisting of chronic bronchitis, allergic rhinitis, and adult respiratory distress syndrome.

16. The method, according to claim 12, wherein said disease state is capable of being modulated by TNF inhibition.

17. The method, according to claim 16, wherein said disease state is an inflammatory disease or autoimmune disease.

18. The method, according to claim 17, wherein said disease state is selected from the group consisting of joint inflammation, arthritis, rheumatoid arthritis, rheumatoid spondylitis and osteoarthritis, sepsis, septic shock, endotoxic shock, gram negative sepsis, toxic shock syndrome, acute respiratory distress syndrome, cerebral malaria, chronic pulmonary inflammatory disease, pulmonary sarcoidosis, asthma, bone resorption diseases, reperfusion injury, graft vs host reaction, allograft rejection, malaria, myalgias, HIV, AIDS, ARC, cachexia, Crohn's disease, ulcerative colitis, pyresis, systemic lupus erythematosus, multiple sclerosis, type 1 diabetes mellitus, psoriasis, Bechet's disease, anaphylactoid purpura nephritis, chronic glomerulonephritis, inflammatory bowel disease, and leukemia.

19. The method, according to claim 18, wherein said disease state is asthma.

20. The method, according to claim 14, wherein said pathological condition is asthma.

21. The method, according to claim 18, wherein said disease state is selected from the group consisting of acute respiratory distress syndrome, pulmonary inflammatory disease, and pulmonary sarcoidosis.

22. The method, according to claim 18, wherein said disease state is joint inflammation.

23. The method, according to claim 13, wherein said disease state is a disease or disorder of the brain.

24. The method, according to claim 23, wherein said disease state is selected from the group consisting of brain trauma, stroke, ischaemia, Huntingdon's disease, and tardive dyskinesia.

25. The method, according to claim 16, wherein the disease state is a yeast or fungal infection.

26. A method for providing gastroprotection, wherein said method comprises administering an effective amount of a compound of claim 1.

27. A method for providing an analgesic, an anti-tussive, or an anti-hyperalgesic in the treatment of neurogenic inflammatory disease associated with inflammation and pain, wherein said method comprises administering an effective amount of a compound of claim 1.

28. A method for treating asthma which comprises administering an effective amount of a compound of claim 1, in coadministration with a drug selected from the group consisting of bronchodilators, steroids, and xanthines.

* * * * *

UNITED STATES PATENT AND TRADEMARK OFFICE
CERTIFICATE OF CORRECTION

PATENT NO. : 5,804,588
DATED : September 8, 1998
INVENTOR(S) : Dyke et al.

It is certified that error appears in the above-identified patent and that said Letters Patent is hereby corrected as shown below:

Column 26, line 36: "C(=NOH)$R_7$ CN" should read C(=NOH)$R_7$, CN.

Column 27, line 14: S(O)$_n R_{11}$" should read --S(O)$_n R_{11}$--.

Column 29, line 13: "8-difluoromethoxyquinaidine-5" should read --8-difluoromethoxyquinaldine-5--.

Signed and Sealed this

Twelfth Day of January, 1999

Attest:

Attesting Officer

*Acting Commissioner of Patents and Trademarks*